(12) United States Patent
Willcox et al.

(10) Patent No.: US 7,282,214 B2
(45) Date of Patent: Oct. 16, 2007

(54) BIOMEDICAL DEVICES WITH ANTIMICROBIAL COATINGS

(75) Inventors: Mark Willcox, Balmain (AU); Emma Hume, Bronte (AU); Nerida Cole, Lakemba (AU); Yulina Aliwarga, Bondi Junction (AU); Zanini Diana, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 667 days.

(21) Appl. No.: 10/325,255

(22) Filed: Dec. 19, 2002

(65) Prior Publication Data

US 2004/0126409 A1 Jul. 1, 2004

(51) Int. Cl.
| | |
|---|---|
| *G02C 7/04* | (2006.01) |
| *A61K 9/00* | (2006.01) |
| *A61L 28/00* | (2006.01) |
| *A61L 31/00* | (2006.01) |
| *A61F 2/00* | (2006.01) |
| *A61F 2/01* | (2006.01) |
| *A61F 2/02* | (2006.01) |
| *A61F 13/00* | (2006.01) |

(52) U.S. Cl. ............ 424/429; 424/400; 424/422; 424/423; 424/427; 424/430; 424/445; 424/447; 530/300; 530/324; 530/326; 530/327; 514/2; 514/12; 514/13; 514/14

(58) Field of Classification Search .......... None
See application file for complete search history.

(56) References Cited

U.S. PATENT DOCUMENTS

| | | | |
|---|---|---|---|
| 5,472,703 A | 12/1995 | Vanderlaan et al. | |
| 6,719,929 B2 * | 4/2004 | Winterton et al. ........... 264/1.7 |
| 2001/0045676 A1 * | 11/2001 | Winterton et al. ........... 264/2.5 |
| 2004/0121939 A1 * | 6/2004 | Diana ........................... 514/2 |
| 2004/0126409 A1 * | 7/2004 | Willcox et al. ............. 424/429 |
| 2004/0135967 A1 * | 7/2004 | Carney et al. .............. 351/159 |
| 2005/0008676 A1 * | 1/2005 | Qiu et al. ................... 424/429 |

FOREIGN PATENT DOCUMENTS

| | | |
|---|---|---|
| EP | 0 990 924 | 4/2000 |
| WO | WO98/40091 | 9/1998 |
| WO | WO 01/56627 | 8/2001 |
| WO | WO 02/064183 | 8/2002 |
| WO | WO 02/064183 A1 * | 8/2002 |

OTHER PUBLICATIONS

Aliwarga, Y. et al., "Antimicrobial peptides: a potential role in ocular therapy", Clinical and Experimental Ophthalmology, Blackwell Science, AU, vol. 29, No. 3, Jun. 2001, pp. 157-160.
Boman, H.G. et al., "Antibacterial and antimalarial properties of peptides that are cecropin-melittin hybrids", Febs Letters, Elsevier Science Publishers, Amsterdam, NL, vol. 259, No. 1, Dec. 1989, pp. 103-106.
PCT International Search Report, dated Apr. 25, 2005, for PCT Int'l. Appln. No. PCT/US03/40675.
U.S. Appl. No. 09/516,636, filed Mar. 1, 2000, Johnson & Johnson.
Subbalakshmi et al., "Biological activities of C-terminal 15-residue synthetic fragment of melittin: deign of an analog with improved antibacterial activity" FEBS Letters, 448, pp. 62-66 (1999).
Juvvadi et al., "Synthetic Melittin, Its Entantio, Retro, and Retroenantio Isomers, and Selected Chimeric Analogs: Their Antibacterial, Hemolytic, and Lipid Bilayer Action" J. Am. Chem. Soc., vol. 118, pp. 8989-8997 (1996).
Mor et al., "The Vertebrate Peptide Antibiotics Dermaseptins Have Overlapping Structural Features but Target Specific Microorganisms" J. Biol. Chem, vol. 269, pp. 31635-31641 (1994).
Aliwarga et al., "Antimicrobial peptides: a potential role in ocular therapy" Clin. Exp. Ophthalmol., vol. 29, pp. 157-160 (2001).
Boman et al., "Antibacterial and antimalarial properties of peptieds that are cecropin-melittin hybrids" FEBS Letters, vol. 259, pp. 103-106 (1989).
Nos-Barbera et al., "Effect of Hybrid Peptides of Cecropin A and Melittin in an Experimental Model of Bacterial Keratitis" Cornea, vol. 259, pp. 101-106 (1996).
Wold, F., Posttranslation Protein Modifications: Perspectives and Prospects, pp. 1-12 in Posttranslational Covalent Modification of proteins, B. C. Johnson, Ed., Academic Press, New York (1983).
Seifter et al., "Analysis for Protein Modifications and Nonprotein Cofactors" (1990), *Meth. Enzymol.* 182, 626-646.
Rattan et al., "Protein Synthesis: Posttranslational Modifications and Aging", (1992) Ann. N.Y. Acad. Sci. 663, 48-62.

* cited by examiner

*Primary Examiner*—Cecilia J. Tsang
*Assistant Examiner*—Andrew D. Kosar
(74) *Attorney, Agent, or Firm*—Karen Harding (57) ABSTRACT

Biomedical devices with antimicrobial coatings are provided. One or more surfaces of the device are coated with a cationic peptide, cationic proteins, or mixtures thereof to impart antimicrobial properties to the surface.

15 Claims, 1 Drawing Sheet

Figure 1

SEQUENCE LISTING

<160> NUMBER OF SEQ ID NOS: 6

<210> SEQ ID NO 1
<211> LENGTH: 12
<212> TYPE: PRT
<213> ORGANISM: Artificial Sequence
<220> FEATURE:
<223> OTHER INFORMATION: Synthetic Peptides

<400> SEQUENCE: 1

Thr Leu Ile Ser Trp Ile Lys Asn Lys Arg Lys Gln
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Synthetic Peptides

<400> SEQUENCE: 2

Arg Pro Arg Val Ser Arg Arg Arg Arg Arg Gly Gly Arg Arg Arg
1               5                   10                  15

Arg

<210> SEQ ID NO 3
<211> LENGTH: 29
<212> TYPE: PRT
<213> ORGANISM: Artificial Sequence
<220> FEATURE:
<223> OTHER INFORMATION: Synthetic  Peptides

<400> SEQUENCE: 3

Thr Leu Ile Ser Trp Ile Lys Asn Lys Arg Lys Gln Arg Pro Arg Val
1               5                   10                  15

Ser Arg Arg Arg Arg Arg Arg Gly Gly Arg Arg Arg Arg
            20                  25

<210> SEQ ID NO 4
<211> LENGTH: 29
<212> TYPE: PRT
<213> ORGANISM: Artificial Sequence
<220> FEATURE:
<223> OTHER INFORMATION: Synthetic  Peptides

<400> SEQUENCE: 4

Arg Pro Arg Val Ser Arg Arg Arg Arg Arg Gly Gly Arg Arg
1               5                   10                  15

Arg Thr Leu Ile Ser Trp Ile Lys Asn Lys Arg Lys Gln
            20                  25

<210> SEQ ID NO 5
<211> LENGTH: 32
<212> TYPE: PRT
<213> ORGANISM: Oncorhynchus keta

<400> SEQUENCE: 5

Pro Arg Arg Arg Ser Ser Ser Arg Pro Val Arg Arg Arg
1               5                   10                  15

Pro Arg Val Ser Arg Arg Arg Arg Arg Gly Gly Arg Arg Arg Arg
            20                  25                  30

```
<210> SEQ ID NO 6
<211> LENGTH: 26
<212> TYPE: PRT
<213> ORGANISM: Apis florea

<400> SEQUENCE: 6

Gly Ile Gly Ala Ile Leu Lys Val Leu Ala Thr Gly Leu Pro Thr Leu
1               5                   10                  15

Ile Ser Trp Ile Lys Asn Lys Arg Lys Gln
            20                  25
```

BIOMEDICAL DEVICES WITH ANTIMICROBIAL COATINGS

FIELD OF THE INVENTION

This invention relates to coated devices. In particular, the invention provides biomedical devices on the surfaces of which antimicrobial coatings of a synthetic cationic peptide are formed.

REFERENCE TO A SEQUENCE LISTING

A sequence listing is attached hereto and incorporated by reference, in its entirety.

BACKGROUND OF THE INVENTION

Devices for use in and on the human body are well known. The chemical composition of the surfaces of such devices plays a pivotal role in dictating the overall efficacy of the devices. Additionally, it is known that providing such devices with an antimicrobial surface is advantageous.

A wide variety of bactericidal and bacteriostatic coatings have been developed. For example, cationic antibiotics, such as polymyxin, vancomycin, and tetracycline have been used as coatings for contact lenses. Further, metal chelating agents, substituted and unsubstituted polyhydric phenols, aminophenols, alcohols, acid and amine derivatives, and quarternary ammonium have been used as antimicrobial agents for contact lenses. U.S. Pat. No. 5,472,703 discloses certain lipid compounds as antimicrobial agents for contact lenses.

However, the use of these known antimicrobial coatings has disadvantages. With the use of antibiotic coatings, microorganisms resistant to the antibiotics may develop. Chelating agent use fails to address the numbers of bacteria that adhere to the device. Some of the prior art coatings, for example phenol derivatives and cresols, can produce ocular toxicity or allergic reactions. Quarternary ammonium compounds are problematic because of their irritancy. Thus, a need exists for safe and effective antimicrobial coatings that overcomes at least some of these disadvantages.

U.S. Ser. No. 09/516,636 discloses that protamine, melittin, cecropin A, nisin, or combinations thereof, may be used as surface coatings to reduce adherence of bacteria to a device's surface and/or reduce growth of bacteria adhered to a device. Unfortunately those peptides have been found to be toxic in certain concentrations or have a limited spectrum of antimicrobial activity.

Subbalakshmi et al., FEBS Letters, 448, pgs. 62–66 (1999) discloses that the C-terminal 15 amino acid residues of melittin, retain their antibacterial activity but has greatly reduced haemolytic activity. Juvvadi et al. disclose placing the C-terminal of melittin at the N-terminal of synthetic peptides reduced mammalian cell cytotoxicity (Juvvadi et al., J. Am. Chem. Soc., vol. 118, pgs. 8989–8997 (1996)). However, the range of bacteria that were inhibited by the C-terminal peptide were decreased and the amount of peptide needed to inhibit those bacteria was increased (Subbalakshmi et al., FEBS Letters, 448, pgs. 62–66 (1999)).

Mixtures of cationic peptides have also been disclosed. For example, synthetic peptides containing lysine as the cationic moiety have been synthesized (Mor et al., J. Biol. Chem, vol. 269, pgs. 31635–31641 (1994)) as has a mixture of protamine and melittin (Aliwarga et al., Clim. Exp. Ophthalmol., vol. 29, pgs. 157–160 (2001)).

Synthetic peptides that incorporate the active moieties from different cationic peptides in one single molecule have also been synthesized. For example, a series of peptides made from combinations of cecropin A and melittin were disclosed to retain most of their antibacterial efficacy (Boman et al., FEBS Letters, vol. 259, pgs. 103–106 (1989)). A hybrid of cecropin A and melittin was also synthesized and disclosed to reduce signs of infection and inflammation in an experimental model of microbial keratitis (Nos-Barbera et al., Cornea, vol. 259, pgs, 101–106 (1996)). However, the toxic regions of melittin were also retained and would be expected to induce toxicity in mammalian cells.

DETAILED DESCRIPTION OF THE INVENTION AND PREFERRED EMBODIMENTS

The present invention provides biomedical devices with an antimicrobial coating and processes for the production of the biomedical devices. It is an unexpected discovery of the invention that certain synthetic peptides may be used to provide antimicrobial coatings for biomedical devices. Specifically, the synthetic antimicrobial peptides of the present invention comprise the 15–26 segment of mellitin, segment A:

SEQ ID NO: 1 and the 1–17 segment of protamine, segment B:

SEQ ID NO: 2 present anywhere in a peptide. The peptides may further comprise a third segment C, which may be any linking group which does not inhibit the antimicrobial activity of the peptide or induce toxicity in mammalian cells, and which includes spacers of 0 to about 10 amino acids. Amino acids, as defined herein, refer to any structure with the chemical formula —HN—$(CR^jR^2)_n$—CO— wherein n is an integer between 1 and 21, $R^1$ and $R^2$ are independently selected from the group consisting of H, straight or branched alkyl groups having 1 to 4 carbon atoms, straight or branched hydroxy groups having 1–2 carbon atoms, straight or branched alkylthio groups having 1 to 3 carbon atoms, carbamoyl groups having 1 to 3 carbon atoms, carboxy groups having 1 to 3 carbon atoms, primary and secondary amino groups having 1 to 4 carbon atoms and 1 to 3 nitrogen atoms, benzyl, phenol, phenyl indoles and N,N-pyrroles. Preferably n is an integer between 1 and 10 and at least one of $R^1$ and $R^2$ is H and the other is selected from the above. The A, B and C segments of the antimicrobial synthetic peptide may be in any order and may be repeated in part or whole. In a preferred embodiment, the A and B segments are in terminal positions and in another preferred embodiment the synthetic antimicrobial peptide has the formula ACB or BCA and C comprises up to 5 amino acids.

The invention also includes synthetic antimicrobial peptides that are conservative variations of those peptides exemplified herein. The term "conservative variation" as used herein denotes a polypeptide in which at least one amino acid is replaced by another, biologically similar residue. Examples of convservative variations include the substitution of one hydrophobic residue, such as isoleucine, valine, leucine, alanine, cysteine, glycine, phenylalanine, proline, tryptophan, tyrosine, norleucine or methionine for another, or the substitutions of one polar residue for another such as the substitution of arginine for lysine, glutamic acid for aspartic acid or glutamine for asparagine and the like. Neutral hydrophilic amino acids that can be substituted for one another include asparagine, glutamine, serine and threonine.

In particular, it is one discovery of the invention that melimine, protattin and mixtures thereof when used as surface coatings, reduces adherence of bacteria to a device's surface, reduces growth of bacteria adhered to a device, or both by greater than about 40 percent.

In one embodiment, the invention provides a biomedical device comprising, consisting essentially of, and consisting of at least one surface comprising, consisting essentially of, and consisting of a coating effective amount of at least one synthetic antimicrobial peptide. In yet another embodiment, a method for manufacturing biomedical devices comprising, consisting essentially of, and consisting of contacting at least one surface of a biomedical device with a coating effective amount of at least one synthetic antimicrobial peptide is provided. In still another embodiment of the invention, a second method for the manufacturing of biomedical devices comprising, consisting essentially of, and consisting of contacting at least one surface of a biomedical device with a coating effective amount of at least one synthetic antimicrobial peptide is provided. In yet another embodiment the present invention provides a method for manufacturing a biomedical device comprising, consisting essentially of, and consisting of adding at least one polymerizable synthetic antimicrobial peptide to a reactive mixture and polymerizing said reactive mixture to form a biomedical device.

By "biomedical device" is meant any device designed to be used while in or on either or both human tissue or fluid. Examples of these devices include but are not limited to catheters, implants (including, but not limited to heart valves), stents, fluid collection bags, sensors, hydrogel bandages, tubing, carriers for antibiotic, diagnostic and therapeutic agents, and ophthalmic devices. In some embodiments catheters are a preferred medical device. A class of preferred biomedical devices includes ophthalmic devices, particularly contact lenses.

As used herein, the terms "lens" and "opthalmic device" refer to devices that reside in or on the eye. These devices can provide optical correction, wound care, drug delivery, diagnostic functionality or may be cosmetic. The term lens includes but is not limited to soft contact lenses, hard contact lenses, intraocular lenses, overlay lenses, ocular inserts, and optical inserts.

In a preferred embodiment, the biomedical device is an ophthalmic lens including, without limitation, contact or intraocular lenses. More preferably, the device is a contact lens, most preferably a soft contact lens.

The term "peptide" or "polypeptide", as used herein, refers to the basic chemical structure of polypeptides that is well known and has been described in textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types. It will be appreciated that polypeptides often contain amino acids other than the 20 amino acids commonly referred to as the 20 naturally occurring amino acids, and that many amino acids, including the terminal amino acids, can be modified in a given polypeptide, either by natural processes, such as processing and other post-translational modifications, or by chemical modification techniques which are well known to the art. Even the common modifications that occur naturally in polypeptides are too numerous to list exhaustively here, but they are well described in basic texts and in more detailed monographs, as well as in a voluminous research literature, and they are well known to those of skill in the art. Among the known modifications which can be present in polypeptides of the present are, to name an illustrative few, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance PROTEINS—STRUCTURE AND MOLECULAR PROPERTIES, 2nd Ed., T. E. Creighton, W. H. Freeman and Company, New York (1993). Many detailed reviews are available on this subject, such as, for example, those provided by Wold, F., Posttranslational Protein Modifications: Perspectives and Prospects, pgs. 1–12 in POST-TRANSLATIONAL COVALENT MODIFICATION OF PROTEINS, B. C. Johnson, Ed., Academic Press, New York (1983); Seifter et al., (1990), *Meth. Enzymol.* 182, 626–646 and Rattan et al., "Protein Synthesis: Posttranslational Modifications and Aging", (1992) Ann. N.Y. Acad. Sci. 663, 48–62. It will be appreciated, as is well known and as noted above, that polypeptides are not always entirely linear. For instance, polypeptides (both linear and non-linear) can be generated as a result of posttranslational events, including natural processing event and events brought about by human manipulation which do not occur naturally. Circular, branched and branched circular polypeptides can be synthesized by non-translation natural process and by entirely synthetic methods, as well. Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications can be present in polypeptides of the present invention, as well. For instance, the amino terminal residue of polypeptides made in *E. coli* or other cells, prior to proteolytic processing, almost invariably will be N-formylmethionine. During post-translational modification of the peptide, a methionine residue at the $NH_2$-terminus can be deleted. Accordingly, this invention contemplates the use of both the methionine-containing and the methionineless amino terminal variants of the protein of the invention. The modifications that occur in a polypeptide often will be a function of how it is made. For polypeptides made by expressing a cloned gene in a host, for instance, the nature and extent of the modifications in large part will be determined by the host cell posttranslational modification capacity and the modification signals present in the polypeptide amino acid sequence. For instance, as is well known, glycosylation often does not occur in bacterial hosts such as, for example, *E. coli*. Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to express efficiently mammalian proteins having native patterns of glycosylation, inter alia. Similar considerations apply to other modifications. It will be appreciated that the same type of modification can be present in the same or varying degree at several sites in a given polypeptide. Also, a given polypeptide can contain many types of modifications. In general, as used herein, the term polypeptide encompasses all such modifications, particularly those that are present in polypeptides synthesized recombinantly by expressing a polynucleotide in a host cell.

As used herein "Melimine" refers to a polypeptide comprising an amino acid sequence of SEQ ID NO: 3. As used herein, L-melimine comprises the above amino acid sequence as it exists naturally. Optical isomers of amino acids undergo spontaneous nonenzymatic racemisation. This rate varies for each amino acid at a given temperature or pH (storage conditions), but is more rapid in D than L isomers. As used herein L- or D-peptides will comprise about 99% L or D isomers, respectively at a pH of 7 and a temperature of about 25° C.

L-amino acids are the naturally occurring form in biological systems, therefore D-isomers are more resistant to enzymatic breakdown and may have an increased persistance. This property may be exploited by the use of mixtures of the stereoisomers to give desired levels of activity and longevity for a particular application. So, for applications where long term persistence is desired, the use of a stereoisomeric mixture having a predominance (greater than about 50% and preferably greater than about 70%) D isomer may be preferred. Where greater antibacterial activity is desired the use of a stereoisomeric mixture having a predominance (greater than about 50% and preferably greater than about 70%) L isomer may be preferred.

As used herein "Protattin" refers to a polypeptide comprising an amino acid sequence of SEQ ID NO: 4

Wherein the amino acids are as defined above.

For purposes of the invention, generally the cationic peptide used is substantially purified.

As used herein, the term "substantially purified" means that the protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals that are involved in the synthesis of the protein. Accordingly such preparations of the protein have less than about 30%, 20%, 10%, 5% (by dry weight) of chemical precursors or compounds other than the polypeptide of interest.

Synthetic antimicrobial peptides useful in the invention can be synthesized chemically using standard peptide synthesis techniques. Alternatively, synthetic antimicrobial peptides useful in the present invention can be synthesized in an in vitro translation and/or transcription system.

Synthetic antimicrobial peptides may be synthesized using conventional solid-phase peptide and solution peptide synthesis protocols. Such methods are well known to those skilled in the art. What follows is a descriptive way of making a synthetic antimicrobial petide using the solid phase synthetic technique, but in no way limits the scope of this invention to this method. The synthesis may be performed on any suitable synthetic resin. Suitable resins include insoluble cross-linked polystyrene resin and the like. The amino acids are generally protected using fluorenylmethoxycarbonyl groups and the like and activated with N-hydroxybenzotriazole and, but not necessarily, diisopropylcarbodiimide (DIC) to facilitate their coupling. The completed peptide is cleaved from the resin using, but not limited to trifluoroacetic acid or ammonia, and the resulting material purified by reverse-phase high-performance liquid chromatography (HPLC) and/or dialysis, after which candidate material is freeze-dried from a water/acetonitrile mixture to a dry powder.

Synthetic antimicrobial peptides useful in the invention can also be produced using an in vitro translation and/or transcription system. Such methods are known to those skilled in the art. For example, synthetic mRNA encoding a Melimine or Protattin can be efficiently translated in various cell-free systems, including but not limited to wheat germ extracts and reticulocyte extracts. Alternatively, synthetic DNA comprising the coding sequence for a Melimine or Protattin under the control of a T7 promoter can be efficiently transcribed and translated, in an in vitro transcription and translation system, such as the TNT T7 coupled Reticulocyte Lysate System, which is commercially available from Promega. The resulting polypeptide can be purified by method described herein.

L-melimine, protattin, or combinations thereof may be adsorbed to polymer surfaces of a biomedical device. The synthetic antimicrobial peptides may be used on any surface, but most advantageously are used with negatively charged surfaces.

Alternatively, the synthetic antimicrobial peptides may be functionalized with acryloyl or methacryloyl groups) that can be added into the monomer mix which is then reacted to form a biomedical device having synthetic antimicrobial peptide in the bulk of the polymer forming the device, as well as on the device's surface.

The synthetic antimicrobial peptides alternatively may be bound to the polymer surfaces. This may be either a direct reaction or, preferably, a reaction in which a coupling agent is used. For example, a direct reaction may be accomplished by the use of a reagent of reaction that activates a group in the surface polymer or the synthetic antimicrobial peptide making it reactive with a functional group on the peptide or polymer, respectively, without the incorporation of a coupling agent. For example, one or more amine or alcohol or thiol groups on the synthetic antimicrobial peptide may be reacted directly with isothiocyanate, acyl azide, N-hydroxysuccinimide ester, pentafluorophenoxy ester, sulfonyl chloride, an aldehyde, glyoxal epoxide, carbonate, aryl halide, imido ester, tosylate ester or an anhydride group on the polymer.

In an alternative embodiment, coupling agents may be used. Coupling agents useful for coupling the cationic peptide or protein to the device's surface include, without limitation, N, N'-carbonyldiimidazole, carbodiimides such as 1-ethyl-3-(3-dimethylaminopropyl)carbodiimide ("EDC"), dicyclohexyl carbodiimide, 1-cylcohexyl-3-(2-morpholinoethyl)carbodiimide, diisopropyl carbodiimide, or mixtures thereof. The carbodiimides also may be used with N-hydroxysuccinimide or N-hydroxysulfosuccinimide to form esters that can react with amines to form amides.

Amino groups also may be coupled to the polymer by the formation of Schiff bases that can be reduced with agents such as sodium cyanoborohydride and the like to form hydrolytically stable amine links. Coupling agents useful for this purpose include, without limitation, N-hydroxysuccinimide esters, such as dithiobis(succinimidylpropionate), 3,3'-dithiobis(sulfosuccinimidylpropionate), disuccinimidyl suberate, bis(sulfosuccinimidyl) suberate, disuccinimidyl tartarate and the like, imidoesters, including, without limitation, dimethyl adipimate, difluorobenzene derivatives, including without limitation 1,5-difluoro-2,4-dinitrobenzene, bromofunctional aldehydes, including without limitation gluteraldehyde, and bis epoxides, including without limitation 1,4-butanediol diglycidyl ether. One ordinarily skilled in the art will recognize that any number of other coupling agents may be used depending on the functional groups present on the device's surface.

One ordinarily skilled in the art also will recognize that, if the device's surface does not contain suitable reactive groups, such suitable groups may be incorporated into the polymer by any conventional organic synthesis methods. Alternatively, the reactive groups may be introduced by the addition of polymerizable monomers containing reactive groups into the monomer mixture used to form the polymer.

Examples of polymer surfaces onto which the synthetic antimicrobial peptides may be adsorbed or bonded are surfaces formed from, without limitation, polymers and copolymers of styrene and substituted styrenes, ethylene, propylene, acrylates and methacrylates, N-vinyl lactams, acrylamides and methacrylamides, acrylonitrile, acrylic and methacrylic acids as well as polyurethanes, polyesters, polydimethylsiloxanes and mixtures thereof. Such polymers may include hydrogels and silicone hydrogels. Preferably, lightly crosslinked polymers and copolymers of 2-hydroxyethylmethacrylate ("HEMA") are used. By "lightly crosslinked" is meant that the polymer has a low enough crosslink density so that it is soft and elastic at room temperature. Typically, a lightly crosslinked polymer will have about 0.1 to about 1 crosslinking molecule per about 100 repeating monomer units. Examples of suitable lightly crosslinked HEMA polymers and copolymers include without limitation, etafilcon A and copolymers of glycerol methacrylate and HEMA. Also preferably, silicone hydrogels, especially those of hydrophilic monomers, such as N,N-dimethylacrylamide, are used.

In one embodiment of the process for making the device of the invention, the surface to be coated is contacted with the L-melimine, protattin or combinations thereof in any convenient manner. Preferably, the coating comprises L-melimine. For example, the device may be placed in a solution of L-melimine and solvent into which the medical device is placed. As an alternative, the device's surface may first be treated with a coupling agent and the surface then placed in a solution of the selected synthetic antimicrobial peptide. As yet another alternative the synthetic antimicrobial peptide may be reacted alone with the polymer surface.

In certain embodiments the free $NH_2$ groups of the synthetic antimicrobial peptides of the present invention are attached to a polymeric surface containing reactive COOH groups.

Suitable solvents for use in the invention are those that are capable of dissolving the selected synthetic antimicrobial peptide, such as L-melimine, protattin singly or in combination. Preferably, the coating process is carried out in water, alcohol, or mixtures thereof. EDC is effective in aqueous solutions and, thus, is a preferred coupling agent.

The coupling agents may be used alone or in combination with agents capable of stabilizing any reactive intermediate formed. For example, EDC may be used with N-hydroxysuccinimide as a stabilizer. Additionally, it may be desirable to adjust the pH. Preferably, the pH is adjusted to about 6.5 to about 8.0, more preferably about 7.0 to about 7.5.

Alternatively, latent reactive components may be added to the monomer mix where the selected polymer does not have suitable carboxylic acid functionality. Suitable latent reactive components include, without limitation, ester compounds of the formula R-CO-L wherein R comprises a group capable of cationic, anionic or free radical polymerization and L is a leaving group. Suitable R groups include monovalent groups that can undergo free radical and/or cationic polymerization comprising up to 20 carbon atoms. Preferred R groups comprise free radical reactive groups, such as acrylates, styryls, vinyls, vinyl ethers, $C_{1-6}$alkylacrylates, acrylamides, $C_{1-6}$alkylacrylamides, N-vinyllactams, N-vinylamides, $C_{2-12}$alkenyls, $C_{2-12}$alkenylphenyls, $C_{2-12}$alkenylnaphthyls, or $C_{2-6}$alkenylphenyl$C_{1-6}$alkyls or a cationic reactive group such as vinyl ethers or epoxide groups and mixtures thereof. Particularly preferred R groups include methacrylates, acryloxys, methacrylamides, acrylamides, and mixtures thereof.

Suitable L groups are stable under reaction conditions, and protect the carboxylate group and leave readily under coating conditions. Suitable L groups include alkyl esters, phenyl esters, hydroxy para-nitroaryls, p-nitrophenyl esters, N-hydroxylamine derivatives, and tosylate esters all of which may be substituted or unsubstituted. Preferred L groups include t-butyl esters, 2,4,5-trichlorophenyl esters, pentafluorophenyl esters, N-hydroxysuccinimide esters, N-hydroxy-oxo-dihydrobenzotriazine derivatives, 1-hydroxybenzotriazole esters and combinations thereof. Preferred suitable L groups include pentafluorophenyl esters, tosylate esters, and N-hydroxysuccinimide esters, and mixtures thereof. Preferred latent reactive compounds include pentafluoromethacrylate and N-acryloxysuccinimide and mixtures thereof and the like.

A coupling effective amount of the selected coupling agent or reactive component is used which amount is an amount sufficient to couple the synthetic antimicrobial peptide to the device surface. The precise amount of coupling agent used will depend on the surface's chemistry as well as the agent selected. Generally, about 0.01 to about 10 weight percent, preferably about 0.01 to about 5.0, more preferably about 0.01 to about 1 weight percent of the coupling agent is used based on the weight of the coating solution. By coating solution is meant the synthetic antimicrobial peptide with one or more of the solvent, coupling agent, buffer, and the like. Typically, the amount of coating solution used per lens will be about 1 ml to about 10 ml, preferably about 1 ml to about 5 ml, more preferably about 1 ml to about 2 ml per lens.

In the processes of the invention, a coating effective amount of synthetic antimicrobial peptide, such as L-melimine, protattin, or combinations thereof is used meaning an amount that when contacted with the surface is sufficient to coat the surface so as to impart the desired antimicrobial properties to the surface. By antimicrobial properties is meant either or both the ability to significantly reduce, meaning by greater than about 50 percent, either or both the amount of bacteria adhering to the surface and the growth of bacteria adhered to the surface. In the case of contact lenses, generally, the amount contacted with the lens is about 1 µg to about 10 mg, preferably about 10 µg to about 1 mg per lens. The amount of coating resulting per contact lens is about 50 to about 1000 µg. In cases in which combinations of L-melimine is used, the amount of L-melimine used preferably is between about 250 µg/lens to about 1000 µg/lens.

Temperature and pressure are not critical to the processes of the invention and the process may be conveniently carried out at room temperature and pressure. The contact time used will be a length of time sufficient to coat the surface to the extent desired. Preferably, contact time is about 60 seconds to about 24 hours.

Following contacting, the surface may be washed with water or buffered saline solution to remove unreacted synthetic antimicrobial peptide and solvent. One ordinarily skilled in the art will recognize that the polymer for pro-ducing the surface to be coated by the method of the invention may contain other monomers and additives. For example, ultra-violet absorbing monomers, reactive tints, processing aids, and the like may be used.

The invention will be further clarified by a consideration of the following, non-limiting examples.

EXAMPLE 1

To assess the effect of cationic proteins/peptides in solution against bacterial cells, *Psudomonas aeruginosa* 6294 and *Staphylacoccus aureus* 31 cells were grown as for 18 hours in Tryptone Soya Broth (TSB) at 35° C. The cells were then harvested by centrifugation and washed twice in phosphate buffered saline (PBS; NaCl 8 g/l; KCl 0.2 g/l; $Na_2HPO_4$ 1.15 g/l; $KH_2PO_4$ 0.2 g/l). The cells were then re-suspended to OD 0. 1 at 660 nm in PBS. The cationic peptide was serially diluted from 1 mg/ml and dilutions were added to wells in a 96 well microtitre plate or into 5 ml disposable test-tubes. Controls were bacteria without peptides. Bacteria were incubated for 18 hours at 35° C. and turbidity was measured at 660 nm. A lack of turbidity in the test-tube corresponding to the peptide dilution was considered to be the minimum inhibitory concentration ("MIC").

TABLE 1

| Peptide | Sequence | S.a. 31 | S.a. CK 5 | P.a 6294 | P.a 15442 |
|---|---|---|---|---|---|
| Melimine | TLISWIKNKRKQRP RVSRRRRRRGGRRRR SEQ ID NO. 3 | 125 | 250 | R | R |
| Prottatin | RPRVSRRRRRRGG RRRRTLISWIKNKRKQ SEQ ID NO. 4 | 1000 | 500 | 500 | 1000 |
| Mellitin (15–26) | TLISWIKNKRKQ SEQ ID NO. 1 | R | R | R | R |
| Protamine (1–17) | RPRVSRRRRRRGGRRRR SEQ ID NO. 2 | R | 1000 | R | R |
| Protamine | PRRRRSSSRPVRRRRRPRV SRRRRRGGRRRR SEQ ID NO. 5 | R | ND | R | ND |
| Mellitin | GIGAILKVLATGLPTLISWIKNKRKQ SEQ ID NO. 6 | 15 | ND | R | ND |

Values expressed as the minimum concentration in µg/ml required to inhibit bacterial growth
R = resistant, highest concentration of peptide = 1000 ug/Ml;
ND = NOT determined
S.a. 31 is *S. aureus* 31
S.a. CK5 is *S. aureus* CK5
P.a 6294 is *P. aeruginosa* 6294
P.a 15442 is *P. aeruginosa* 15442

The data in Table 1 indicate that when measured using the conventional does setting method of the solution tube method, Melimine in solution has an MIC for *S. aureus* of between 60 and 250 µg/ml but that *P. aeruginosa* is resistant to this peptide up to 1000 µg/ml (the highest concentration used).

EXAMPLE 2

For conducting viable counts, Etafilcon A lenses were removed from the manufacturers vials, washed three times in 1 ml PBS, dried and then coated by pipetting 500 μg L-Melimine onto the contact lenses (melimine was dissolved in distilled water and air dried onto contact lenses) overnight at ambient temperature in a fume hood. The number of lenses used for each strain is shown in Table 2 in parenthesis. Lenses were rehydrated in PBS for 10 minutes and 0.5 ml of $1 \times 10^8$ bacterial cells/ml, including gram-positive *S. aureus* and gram-negative *P. aeruginosa* were added to the lenses. After incubation at ambient temperature for either 10 min or 5 hours, the lenses were washed three times in PBS to remove non-adherent or loosely adherent bacteria. Lenses were then homogenized using tissue homogenizer and 1 ml PBS until lens disintegration (about 1–2 minutes). Serial dilutions were then made according to the technique of Miles and Misra and aliquots (20 μL) plated out on nutrient agar. After incubation overnight at 37° C., viable bacteria were determined and results expressed as colony forming units/mm$^2$ after calculation of the surface area of the lens (approximately 310 mm$^2$). The effects are calculated based upon comparison to adhesion control lens that was not coated with cationic protein/peptide before bacterial adhesion testing. The results are shown on Table 2.

TABLE 2

| Bacterial Strain | % reduction at 10 min | % reduction at 5 hrs |
|---|---|---|
| P. aeruginosa 6294 | 44 ± 30 (4) | 95 ± 2 (3) |
| P. aeruginosa 15442 | 31 ± 38 (5) | 78 ± 16 (3) |
| S. aureus 31 | 62 ± 32 (5) | 77 ± 21 (3) |
| S. aureus CK5 | 86 ± 18 (4) | 86 ± 7 (4) |

After both 10 minutes and five hours exposure, L-Melimine was able to significantly reduce the number of bacteria on the hydrogel polymer. The data show the lenses coated with 500 μg of L-Melimine reduced the number of microorganisms adhered to a hydrogel polymer by at least about 80% for the bacteria strains tested.

EXAMPLE 3

Etafilcon lenses, commercially available from Johnson & Johnson as ACUVUE® Brand contact lenses) were soaked as in Example 2, above, except that the L-melimine concentration was varied: 125 μg, 250 μg or 500 μg/lens. After absorption of L-Melimine onto the hydrogel polymer, the lenses were rehydrated with PBS, and exposed to *S. aureus* or *P. aeruginosa* for either 10 minutes or five hours, as described in Example 2. After exposure, the polymer was evaluated for numbers of microorganisms the standard Miles and Misra plate count assay.

The results in Table 3 show that, with a decreased concentration of L-Melimine, there was a corresponding decrease in the numbers of microorganisms that were inhibited.

EXAMPLE 4

Stock solutions (50 mg/ml) were prepared containing the L-Protattin in distilled water. 500 μg of the stock solution was adsorbed to a contact lens made from Etafilcon A as for L-melamine in Example 2 for 18 hours at ambient temperature in a fume hood. The subsequent experimental details are as described in Example 2, above and viable bacteria was measured. Results are shown in Table 4, below.

TABLE 4

| Bacterial Strain | % reduction at 10 min | % reduction at 5 hrs |
|---|---|---|
| P. aeruginosa 6294 | 97 ± 5 (6) | 57 ± 39 (6) |
| P. aeruginosa 15442 | 94 ± 4 (8) | 63 ± 32 (7) |
| S. aureus 31 | 64 ± 18 (6) | 43 ± 33 (6) |
| S. aureus CK5 | 6 ± 62 (7) | 3 ± 25 (7) |

Number of lenses tested shown in ()

The data in Table 4 shows a reduction in microorganisms attached to a hydrogel polymer with the Protattin peptide. However, in comparison with the L-Melimine data in Example 2, the L-Melimine is a preferred order of the amino acid sequences as it was more effective than Protattin at reducing bacterial adhesion and colonisation to contact lenses, particularly after several hours.

EXAMPLE 5

A heat stability study was conducted to evaluate whether post-exposure of the L-Melimine to autoclaving would alter the ability of the peptide to prevent bacterial growth.

Bacteria (*P. aeruginosa* 6294 and *S. aureus* 31) were grown for 18 hours at 35° C. in TSB, then washed twice in PBS. The bacteria were resuspended in PBS to an optical density of 0.1 at 660 nm. L-Melimine was dissolved in PBS to a concentration of 1000 μg/ml and autoclaved at 121° C. for 15 minutes. Equal volumes of bacterial suspension and L-Melimine were then added together and incubated at 35° C. for periods of up to 72 hours. Controls were non-autoclaved L-Melimine. After 24, 48 and 72 hours, aliquots of the bacteria/L-Melimine solutions were removed and the number of viable bacteria were counted using the standard Miles and Misra plate count assay. Tables 5A and 5B show the results.

TABLE 3

| Bacterial Strain | % reduction at 10 min | | | % reduction at 5 hrs | | |
|---|---|---|---|---|---|---|
| | 125 μg | 250 μg | 500 μg | 125 μg | 250 μg | 500 μg |
| P. aeruginosa 6294 | −19 ± 41 (4) | 27 ± 15 (4) | 44 ± 30 (4) | 60 ± 40 (8) | 77 ± 11 (4) | 93 ± 2 (3) |
| S. aureus 31 | −1361 ± 1745 (4) | −127 ± 254 (3) | 62 ± 32 (5) | −81 ± 98 (5) | −163 ± 266 (3) | 77 ± 21 (3) |

Number of lenses tested shown in ( )

TABLE 5A

Heat stability of Melimine in solution against *P. aeruginosa* 6294

| | % inhibition of growth | | |
|---|---|---|---|
| Treatment | @ 24 hours | @ 48 hours | @ 72 hours |
| None | 100 (5) | 100 (3) | 100 (2) |
| Autoclaved | 100 (3) | 100 (3) | 100 (2) |

Number of lenses tested shown in ()

TABLE 5B

Heat stability of Melimine in solution against *S. aureus* 31

| | % inhibition of growth | | |
|---|---|---|---|
| Treatment | @ 24 hours | @ 48 hours | @ 72 hours |
| None | 100 (5) | 100 (3) | 99 (2) |
| Autoclaved | 100 (3) | 100 (3) | 99 (2) |

Number of lenses tested shown in ()

All standard deviations were 1 or less. Autoclave treatment of the L-Melimine did not result in any reduction in activity.

EXAMPLE 6

Bacteria (*Streptococcus pneumoniae* and *Serratia marcescens*) were grown as described in Example 1. Contact lenses were prepared as is Example 2 and allowed to soak in the bacteria solution for 10 minutes. After adhesion, the lenses were processed as described in Example 2 and the % reduction in bacteria as compared to a control lens which was not L-melimine treated was measured. The results are shown in Table 6, below.

TABLE 6

| Bacterial Strain | % reduction at 10 min |
|---|---|
| *S. pneumoniae* | 68 ± 7 (3) |
| *S. marcescens* | 43 ± 36 (4) |

Number of lenses tested shown in ()

The data in Table 6 shows that L-Melimine was able to reduce the adhesion of *S. pneumoniae* and *S. marcescens* to contact lenses. These bacteria have been isolated from contact lenses at the time of an adverse event.

EXAMPLE 7

Three contact lenses (Etafilcon A) were washed twice in 0.1M sodium acetate buffer pH 5.0 then resuspended in 2 ml 0.1M sodium acetate buffer pH 5.0 with 1-ethyl-3-(3-dimethylaminopropyl) carbodiimide hydrochloride ("EDC") at a final concentration of 2 mg/ml in sodium acetate buffer pH 5.0 and allowed to react for 15 minutes at room temperature. Contact lenses were then washed three times in PBS pH 7.4. Contact lenses were then resuspended in 1 mg/ml L-Melimine in PBS and incubated for two hours at 37° C. with mixing. The contact lenses were washed four times in PBS and the bound peptide quantified by a method developed by Cole and Ralston (1994). Contact lenses were stained for 2–24 hours using filtered 0.025% Coomassie stain in 10% acetic acid and 10% iso-propanol at 37° C. Lenses were destained in 10% acetic acid and 10% iso-propanol at 37° C. Lenses were then extracted in 25% Pyridine overnight. The extracted solutions were analysed in the spectrophotometer at A600 using 25% Pyridine as a blank. L-Melimine quantification was determined by correlating extracts against a standard curve constructed by pipetting known amounts of L-Melimine on semi-dried acrylamide gels and extracting as above, this method extracts all amounts of peptide from the gel. Approximately 18 µg/lens of Melimine was bound on to contact lenses using this method.

The lenses were exposed to bacteria (*P. aeruginosa* for 10 minutes at 35° C.) and analyzed as described in Example 2. The lenses showed a 66±3% reduction in bacterial adhesion.

EXAMPLE 8

Contact lenses were coated and dried (as in Example 2) and D-Melimine applied at a concentration of either 250 µg per lens or 500 µg per lens. D-melimine was made using D-amino acids as for L-melimine using standard peptide synthesis techniques (e.g. Fmoc). Assays for measuring inhibition of bacterial adhesion were performed as in Example 2.

TABLE 7

| | % Reduction L-melimine | | | |
|---|---|---|---|---|
| Bacterial | % reduction @ 250 µg/lens | | % reduction @ 500 µg/lens | |
| Strain | 10 min | 5 hrs | 10 min | 5 hrs |
| *P. aeruginosa* 6234 | 27 + 15 (4) | 77 + 11 (4) | 44 + 30 (4) | 93 + 2 (3) |
| *S. aureus* 31 | 127 + 2 54 (3) | 163 + 266 (3) | 62 + 32 (5) | 77 + 21 (3) |

TABLE 8

| | % reduction D-melimine | | | |
|---|---|---|---|---|
| Bacterial | % reduction @ 250 µg/lens | | % reduction @ 500 µg/lens | |
| Strain | 10 min | 5 hrs | 10 min | 5 hrs |
| *P. aeruginosa* 6234 | 22 + 49 (4) | 82 + 16 (5) | 66 + 36 (2) | 81 + 11 (2) |
| *S. aureus* 31 | 641 + 54 8 (4) | 621 + 433 (5) | 495 + 67 7 (2) | 1761 + 25 99 (2) |

At ten minutes and 250 µg/lens both L- and D-Melimines had little statistically measurable activity towards *S. aureus* (Tables 7 and 8). Additionally, there was no difference in activity against *P. aeruginosa* for the D-enantiomer at 250 µg/lens in comparison with the L-Melimine. At a concentration of 500 µg/lens, the L-entiomer showed activity against both *P. aeruginosa* and *S. aureus*, while D-enantiomer showed statistically consistent activity towards *P. aueruginosa*.

EXAMPLE 9

For in vitro cytotoxic testing, solutions of L-Melimine were prepared in PBS (500 µg/ml, 250 µg/ml, 125 µg/ml and 62.5 µg/ml). Solutions were then diluted 1:3 in tissue culture media (EMEM) and added to murine L929 cells for 48 hours. Cells are rinsed in saline then harvested using 0.25% trypsin for 3–5 minutes at ambient temperature. 1 ml of saline is then added to cells and trypsin mixture, a 500 µl aliquot is added to 19.5 ml of saline and counted in a coulter counter in triplicate. Results are compared to unperturbed cultures as well as positive (cyotoxic) controls. Results are expressed as percentage of non-viable cells (100-number of cells in sample/number of cells in unperturbed cells×100). In addition, the ability of the peptides to lyze sheep red blood cells was examined. The sheep red blood cells were washed and resuspended in PBS. Peptides at various concentrations were added to the red blood cells and incubated at 37° C. for 4 h. 100% lysis was obtained using distilled water and 0% lysis was obtained using PBS. Lysis was measured by measuring the amount of haemoglobin released into the PBS after centrifugation to remove whole red blood cells.

TABLE 9

| L-Melimine conc. (µg/ml) | % cell inhibition |
|---|---|
| 500 | 44 |
| 250 | 26 |
| 125 | 8 |
| 62.5 | 20 |

Figure 1:
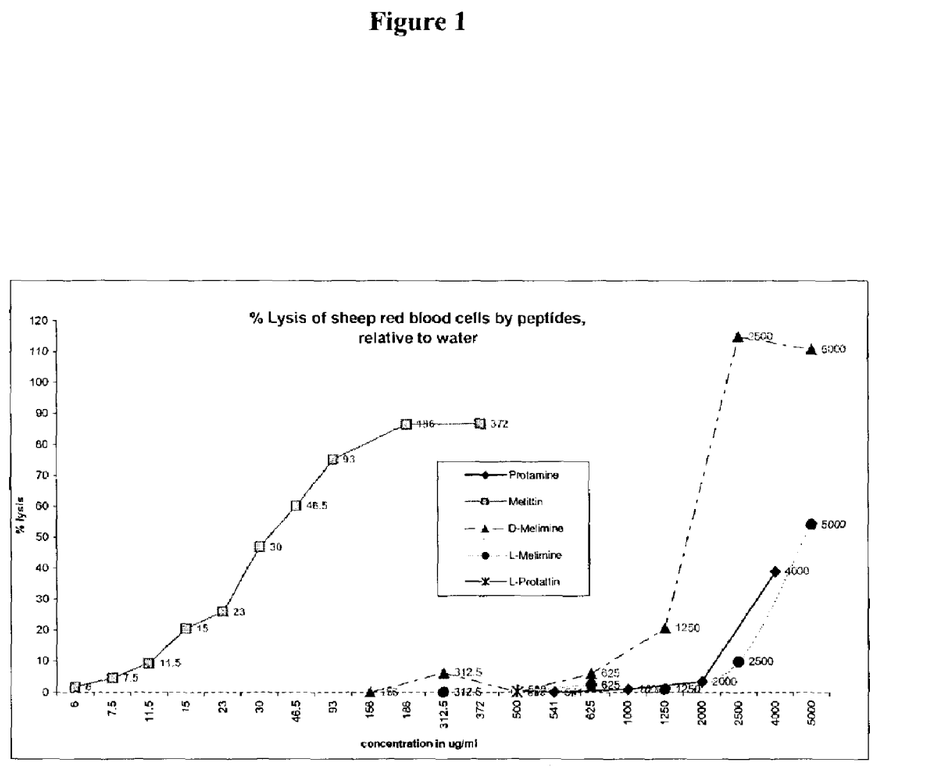
FIG. 1 is a graph showing the % lysis sheep red blood cells relative to water for various peptides.

L-Melimine was found to be marginally cytotoxic at 500 µg/ml and non-cytotoxic at all other concentrations (Table 9). As shown in FIG. 1, Melittin caused extensive hemolysis of red blood cells, whereas all other peptides/proteins caused much less hemolysis. L-Melimine caused the least amount of hemolysis of any peptide/protein. These results indicate that Melimine may be used on contact lenses without causing an adverse reaction in eyes.

EXAMPLE 10

L-Melimine was evaluated to determine its potential to induce resistance in *P. aeruginosa* and *S. aureus*. Prior to L-Melimine exposure, MICs of both strains were determined as in Example 1. The *P. aeruginosa* strain was resistant at 1 mg/ml in Example 1, so starting concentration to determine the MIC for L-Melimine when incubated with *P. aeruginosa* was raised to 15 mg/ml and the MIC was determined to be 4 mg/ml, using the procedure of Example 1. For the Example 10, about 25% of the MIC was used as the subinhibitory concentration, which is shown in column 2 of Table 10, below. Bacteria were grown overnight in TSB. Bacteria were inoculated 1:100 into fresh TSB containing sub-inhibitory levels of L-Melimine and incubated overnight. Bacteria from the broth containing sub-inhibitory levels (column 2, Table 9) were then re-incubated in fresh TSB with the same concentration of L-Melimine. This was repeated for 30 consecutive days. After passaging, a MIC for the bacteria from the last passage was determined. Any increase in MIC would indicate a potential for bacteria to become resistant.

TABLE 10

| Strain | Sub-inhibitory concentration | MIC prior to passage | MIC post-passage |
|---|---|---|---|
| *P. aeruginosa* | 1 mg/ml | 4 mg/ml | 4 mg/ml |
| *S. aureus* | 30 µg/ml | 125 µg/ml | 63 µg/ml |

The MIC *P. aeruginosa* did not change over time and shows no potential for resistance to Melimine. The MIC for *S. aureus* actually decreased over the passage time, which indicates that in sub-inhibitory levels this strain is becoming more susceptible to this peptide. There is no indication for potential resistance to L-Melimine by either bacterium. Thus, the present invention provides cationic peptides with antibacterial activity and no indication for antibacterial resistance over time. Thus, medical devices which are coated or treated with these peptides would be suitable for applications where repeated or long term use and antibacterial activity are desired.

EXAMPLE 11

L-Melimine was evaluated to determine its able to retain activity in the presence of tears. L-Melimine was incubated in the presence of tears as follows. Holes were punched in nutrient agar plates which were then seeded with bacteria (*P. aeruginosa* 6294 or *S. aureus* 31). Tears pooled from normal human subjects (10 µl) were added into wells and allowed to absorb into the agar for 15 minutes at ambient temperature. L-Melimine was added at a concentration of 125 µg/well. The nutrient agar plates were incubated overnight at 35° C., following incubation, the zone of inhibition was measured and expressed in mm. The results are shown in Table 11, below.

TABLE 11

| | Zone of inhibition (mm) | | |
|---|---|---|---|
| Strain | Tears | L-Melimine | L-Melimine + Tears |
| *P. aeruginosa* | 0 | 6 ± 1 | 6.8 ± 1.8 |
| *S. aureus* | 0 | 7.25 ± 1.9 | 6.9 ± 0.9 |

There was no significant increase or decrease in the activity of L-Melimine when in the presence of tears suggesting that tears do not interfere with the activity of this peptide.

EXAMPLE 12

To a dry container housed in a dry box under nitrogen at ambient temperature was added 30.0 g (0.277 mol) of bis(dimethylamino)methylsilane, a solution of 13.75 ml of a 1M solution of TBACB (386.0 g TBACB in 1000 ml dry THF), 61.39 g (0.578 mol) of p-xylene, 154.28 g (1.541 mol) methyl methacrylate (1.4 equivalents relative to initiator), 1892.13 (9.352 mol) 2-(trimethylsiloxy)ethyl methacrylate (8.5 equivalents relative to initiator) and 4399.78 g (61.01 mol) of THF. To a dry, three-necked, round-bottomed flask equipped with a thermocouple and condenser, all connected to a nitrogen source, was charged the above mixture prepared in the dry box.

The reaction mixture was cooled to 15° C. while stirring and purging with nitrogen. After the solution reaches 15° C., 191.75 g (1.100 mol) of 1-trimethylsiloxy-1-methoxy-2-methylpropene (1 equivalent) was injected into the reaction vessel. The reaction was allowed to exotherm to approximately 62° C. and then 30 ml of a 0.40 M solution of 154.4 g TBACB in 11 ml of dry THF was metered in throughout the remainder of the reaction. After the temperature of reaction reached 30° C. and the metering began, a solution of 467.56 g (2.311 mol) 2-(trimethylsiloxy)ethyl methacrylate (2.1 equivalents relative to the initiator), 3636.6. g (3.463 mol) n-butyl monomethacryloxypropyl-polydimethylsiloxane (3.2 equivalents relative to the initiator), 3673.84 g (8.689 mol) TRIS (7.9 equivalents relative to the initiator) and 20.0 g bis(dimethylamino)methylsilane was added.

The mixture was allowed to exotherm to approximately 38–42° C. and then allowed to cool to 30° C. At that time, a solution of 10.0 g (0.076 mol) bis(dimethylamino)methylsilane, 154.26 g (1.541 mol) methyl methacrylate (1.4 equivalents relative to the initiator) and 1892.13 g (9.352 mol) 2-trimethylsiloxy)ethyl methacrylate (8.5 equivalents relative to the initiator) was added and the mixture again allowed to exotherm to approximately 40° C. The reaction temperature dropped to approximately 30° C. and 2 gallons of THF were added to decrease the viscosity. A solution of 439.69 g water, 740.6 g methanol and 8.8 g (0.068 mol) dichloroacetic acid was added and the mixture refluxed for 4.5 hours to de-block the protecting groups on the HEMA. Volatiles were then removed and toluene added to aid in removal of the water until a vapor temperature of 110° C. was reached.

The reaction flask was maintained at approximately 110° C. and a solution of 443 g (2.201 mol) TMI and 5.7 g (0.010 mol) dibutyltin dilaurate were added. The mixture was reacted until the isocyanate peak was gone by IR. The toluene was evaporated under reduced pressure to yield an off-white, anhydrous, waxy reactive monomer. The macromer was placed into acetone at a weight basis of approximately 2:1 acetone to macromer. After 24 hrs, water was added to precipitate out the macromer and the macromer was filtered and dried using a vacuum oven between 45 and 60° C. for 20–30 hrs.

EXAMPLE 13

A reaction mixture was formed by adding 100 parts of the components shown in Table 12, in the amounts shown in Table 12 with 20 parts 3,7-dimethyl-3-octanol. Specifically, in the following order macromer, Norbloc 7966, diluent, TEGDMA, HEMA, DMA, TRIS, and mPDMS were added to an amber flask. These components were mixed at 170–300 rpm, at 50–55° C., for 90 to 180 minutes. While maintaining mixing, blue HEMA was added and the components mixed for a further 20 to 75 minutes (at 170–300 rpm, 50–55° C.). Still with mixing, PVP was added and the mixture stirred for another 20 to 140 minutes (at 170–300 rpm, 50–55° C.). Lastly, with continual mixing, CGI 1850 (Irgacure 1850) was added.

TABLE 12

| Component | Weight Percent |
|---|---|
| Macromer (Ex 12) | 18.95 |
| TRIS | 14.7 |
| DMA | 27.4 |
| MPDMS | 29.5 |
| NORBLOC | 2.1 |
| CGI 1850 | 1.1 |
| TEGDMA | 1.1 |
| HEMA | 5.3 |

Pentafluorophenyl methacrylate (OPfp) (0.5 wt. %) was added to the reaction mixture. The reaction mixture was mixed vigorously for approximately 10 minutes (or until the solution appeared clear and evenly mixed) and the then degassed, on high vacuum, until no air bubbles were visible in the reaction mixture (about 20 minutes). The reaction mixtures were placed into thermoplastic contact lens molds, and irradiated using Philips TL 20 W/03 T fluorescent bulbs at 50° C., for about 50 minutes in an $N_2$ atmosphere. The lenses were demolded in Dowanol® DPMA (DPMA, commercially available from Aldrich). Lenses were washed up to five times with DPMA. Each wash lasted about 120 minutes. The lenses were individually placed into vials containing 2 mL of a solution with 2.5 mg/mL melimine and 0.05 weight percent of N,N-diisopropylethylamine (DIPEA) in N,N-dimethylformamide (DMF). The vials (containing the lenses and solution) were stoppered with gray butyl stoppers and then incubated in an Incubator/Shaker for 18 hours at 37° C., shaking continuously at 100 rpm.

After incubation, the solvent from each of the vials was removed. Approximately 9 mL of fresh DMF solvent was then added to each vial. After 1 hour, the solvent was removed and fresh DMF solvent was re-added at the same volume. This process was repeated a total of 4 times each at 1 hour intervals. After the fourth solvent change out, the lenses were placed directly into DI water at room temperature and washed 4 times at 1 hour intervals. After the fourth wash, the lenses were placed into packing solution at room temperature for 1 hour and then autoclaved for 30 minutes at 121° C. Lens properties were measured and are shown in Table 13, below.

EXAMPLE 14

Example 13 was repeated except that coupling additives were added to the melimine-containing coating solution and that the concentration of the melimine-coating solution was changed. So, exactly as per Example 13, the lenses after being released and washed in DPMA solvent, were placed into individually into vials containing 3 mL of a solution of 5 mg/mL of N-hydroxybenzotriazole (HOBt) in DMF. Using a calibrated pipettor, 50 µL of diisopropylcarbodiimide (DIC) was added to each vial. After 20 to 60 minutes at room temperature, 1 mL of a 3 mg/mL melimine in DMF solution containing 0.05 weight percent of N,N-diisopropylethylamine (DIPEA) was added to each vial using a calibrated Eppendorf pipettor. The vials were stoppered with gray butyl stoppers. The lenses were then incubated in an Incubator/Shaker for about 19 hours at 37° C. with shaking continuously at 100 rpm.

After incubation, the solvent from each of the vials was removed. Approximately 9 mL of fresh DMF solvent was then added to each vial. After 1 hour, the solvent was removed and fresh DMF solvent was re-added at the same volume. This process was repeated a total of 4 times each at 1 hour intervals. After the fourth solvent change out, the lenses were placed directly into DI water at room temperature and washed 4 times at 1 hour intervals. After the fourth wash, the lenses were placed into packing solution at room temperature for 1 hour and then autoclaved for 30 minutes at 121° C. Lens properties were measured and are shown in Table 13, below. Standard deviations are shown in parenthesis.

TABLE 13

| Property | Control 1 | Ex 13 | Ex 14 |
|---|---|---|---|
| Water Content(%) | 35.1(0.2) | 35.6(0.3) | 35.4(0.2) |
| Modulus(psi) | 113.0(11.9) | 119.9(10.3) | 132.9(13.0) |
| Elongation(%) | 176.5(75.1) | 128.2(67.8) | 213.1(56.6) |
| Tensile Strength(psi) | 93.1(45.8) | 72.4(43.6) | 127.2(35.5) |
| Toughness(psi) | 91.7(60.0) | 53.5(59.0) | 131.0(62.2) |
| DCA (°) | 96(20) | 95(13) | 67(25) |
| Melimine Concentration (ug/lens) | N/A | ≈120 | ≈140 |

EXAMPLE 15

Lenses made in Examples 13 and 14 were removed from vials and washed three times in 5 mL of PBS for 5 minutes each wash. Uncoated and lenses having the same substrate formulation were used as a control. Four lenses were exposed to bacteria (*P. aeruginosa* or *S. aureus*) at 35° C. for the times shown in Table 14, below and analyzed as described in Example 2.

TABLE 14

|  |  | Example 13 | | Example 14 | |
|---|---|---|---|---|---|
|  |  | Mean | SD | Mean | SD |
| P. aeruginosa (% redxn) | | | | | |
| Time | 10 min | 50 | 0 | 45 | 16 |
|  | 5 hrs | 58 | 1.6 | 46 | 17 |
| S. aureus (% redxn) | | | | | |
| Time | 10 min | 34 | 18 | 47 | 31 |
|  | 5 hrs | 32 | 11 | 33 | 27 |

EXAMPLES 16–19

Example 14 was repeated except that the concentrations of the melimine-coating solution and the wash procedure were changed. So, exactly as per Example 14, the lenses after being released and washed in DPMA solvent, were placed into individually into vials containing 3 mL of a solution of 5 mg/mL of N-hydroxybenzotriazole (HOBt) in DMF. Using a calibrated pipettor, 50 μL of diisopropylcarbodiimide (DIC) was added to each vial. After about 60 minutes at room temperature, 1 mL of a melimine-coating solution of various concentration listed in Table 15, in DMF containing 0.05 weight percent of N,N-diisopropylethylamine (DIPEA) was added to each vial using a calibrated Eppendorf pipettor. The vials were stoppered with gray butyl stoppers. The lenses were then incubated in an Incubator/Shaker for about 19 hours at 37° C. with shaking continuously at 100 rpm.

After incubation, lenses were transferred to a 400 mL beaker containing 300 mL of fresh DMF and a magnetic stirrer. The lenses were stirred in the DMF for 1 hour. This process was repeated three more times (four times total). After the fourth solvent change out, the 300 mL of DI water was added to the beaker and the lenses washed a total of four times with DI water. After the fourth wash, the lenses were placed into vials containing packing solution and then autoclaved for 30 minutes at 121° C. Lens properties were measured and are shown in Table 15, below. Standard deviations are shown in parenthesis.

TABLE 15

| Property | Control 2 | Ex 16 | Ex 17 | Ex 18 | Ex 19 |
|---|---|---|---|---|---|
| Coating Solution Conc. (mg/mL) | 0 | 0.75 | 1.50 | 3.00 | 6.00 |
| Water Content (%) | 35.8 (0.3) | N/M | 35.5 (0.3) | 35.6 (0.3) | N/M |
| Modulus (psi) | 95 (8) | N/M | 111 (13) | 107 (8) | 108 (12) |
| Elongation (%) | 134 (70) | N/M | 164 (82) | 161 (66) | 155 (55) |
| Tensile Strength (psi) | 55 (28) | N/M | 80 (43) | 77 (34) | 72 (25) |
| Toughness (psi) | 44 (42) | N/M | 77 (67) | 68 (53) | 59 (39) |
| DCA (°) | N/M | N/M | N/M | N/M | N/M |
| Melimine Conc. (ug/lens) |  | 63 | 128 | 219 | 334 |

N/M indicates not measured.

EXAMPLE 20

Lenses made in Examples 16 to 19 were removed from vials and washed three times in 5 mL of PBS for 5 minutes each wash. Uncoated and lenses having the same substrate formulation were used as a control. Four lenses were exposed to bacteria (P. aeruginosa or S. aureus) at 35° C. for the times shown in Table 16, below and analyzed as described in Example 2. Standard deviations are shown in parenthesis

TABLE 16

|  |  | Ex 16 | Ex 17 | Ex 18 | Ex 19 |
|---|---|---|---|---|---|
| P. aeruginosa (% redxn) | | | | | |
| Time | 10 min. | 5 (33) | 2 (22) | −31 (35) | 5 (19) |
|  | 5 hrs | 37 (12) | 27 (17) | 20 (10) | 27 (33) |
| S. aureus (% redxn) | | | | | |
| Time | 10 min. | −34 (70) | 3 (72) | −17 (57) | −55 (66) |
|  | 5 hrs | −5 (32) | −9 (59) | −17 (38) | −55 (3) |

EXAMPLE 21

To a 100 mL round bottom flask equipped with a magnetic stirrer and containing 0.60 g melimine, was added 50 mL of N,N-dimethylformamide (DMF). The homogeneous solution was stirred, under nitrogen, at 25° C., for 30 minutes. N,N-Diisopropylethylamine (DIPEA, 33 μL) was added to the solution. The solution was placed in an ice bath and stirred, still under nitrogen. After 20 minutes, methacryloyl chloride (19 μL) was added to the solution. The solution was allowed to come to room temperature and monitored by mass spectrometry. After about 20 hours, 19 μL more of methacryloyl chloride was added to the solution and the solution stirred, at room temperature. After about another 20 hours, DMF was evaporated from the flask and the residue dissolved in DI water and dialyzed against 2×4 L of DI-water using dialysis tubing (benzoylated, cellulose dialysis tubing, molecular weight cut off 2,000, available form Sigma). The dialyzed portion was freeze dried to give about 250 mg of methacryloylated melimine as a fluffy white powder.

EXAMPLE 22

Methacryloylated melimine (Example 21, 74.9 mg) was added to 3.12 grams of DMA and the mixture sonicated at 40° C. until all of the melimine appeared to dissolve (about 1 hour). This melimine/DMA solution was used to make a reaction mixture. A reaction mixture was formed by adding 100 parts of the components shown in Table 17, in the amounts shown in Table 17 with 20 parts 3,7-dimethyl-3-octanol. Specifically, in the following order macromer, Norbloc 7966, diluent, TEGDMA, HEMA, melimine/DMA solution, TRIS, and mPDMS were added to an amber flask. These components were mixed at 170–300 rpm, at 50–55° C., for 90 to 180 minutes. While maintaining mixing, blue HEMA was added and the components mixed for a further 20 to 75 minutes (at 170–300 rpm, 50–55° C.). Still with mixing, PVP was added and the mixture stirred for another 20 to 140 minutes (at 170–300 rpm, 50–55° C.). Lastly, with continual mixing, CGI 1850 (Irgacure 1850) was added.

TABLE 17

| Component | Weight Percent |
|---|---|
| Macromer (Ex 12) | 18.95 |
| TRIS | 14.7 |
| Melimine/DMA solution | 27.4 |
| MPDMS | 29.5 |
| NORBLOC | 2.1 |
| CGI 1850 | 1.1 |
| TEGDMA | 1.1 |
| HEMA | 5.3 |

The reaction mixture was degassed, on high vacuum, until no air bubbles were visible in the reaction mixture (about 20 minutes). The reaction mixtures were placed into thermoplastic contact lens molds, and irradiated using Philips TL 20W/03T fluorescent bulbs at 50° C., for about 60 minutes in an $N_2$ atmosphere. After irradiation, the molds were opened and the lenses released in 60% isopropanol/water and then leached in IPA/DI to remove any residual monomers and diluent. Lenses were transferred to vials containing packing solution and then autoclaved for 30 minutes at 121° C. Lens properties were measured and are shown in Table 18.

TABLE 18

| Property | Control 3 | Ex 22 |
|---|---|---|
| Water Content (%) | 37.7(0.3) | 38.7(0.3) |
| Modulus (psi) | 87(9) | 87(6) |
| Elongation (%) | 258(46) | 279(56) |
| Tensile Strength (psi) | 108(27) | 132(42) |
| Toughness (psi) | 131(46) | 166(63) |
| Melimine Concentration (ug/lens) | ≈3 | ≈70 |

EXAMPLE 23

Lenses made in Example 22 were removed from vials and washed three times in 5 mL of PBS for 5 minutes each wash. Lenses having the same substrate formulation, but without the methacryloylated melimine were used as a control. Four lenses were exposed to bacteria (P. aeruginosa or S. aureus) at 35° C. for the times shown in Table 19, below and analyzed as described in Example 2.

TABLE 19

| Time | Mean | SD |
|---|---|---|
| P. aeruginosa (% redxn) | | |
| 10 min. | −13 | 14 |
| 5 hrs | 5 | 36 |
| S. aureus (% redxn) | | |
| 10 min. | −20 | 87 |
| 5 hrs | −31 | 25 |

EXAMPLE 24

To a 500 mL round bottom flask equipped with a magnetic stirrer and containing 3.00 g melimine, was added 120 mL of N,N-dimethylformamide (DMF). The homogeneous solution was stirred, under nitrogen, at 25° C., for about 5 minutes. N,N-Diisopropylethylamine (DIPEA, 170 µL) was added to the solution. The solution was placed in an ice bath and stirred, still under nitrogen. After 30 minutes, methacryloyl chloride (95 µL) was added to the solution. The solution was allowed to come to room temperature. After about 20 hours, the reaction was complete, as monitored by mass spectrometry. DMF was evaporated from the flask and the residue dissolved in about 10 mLs DI water and dialyzed against 3×4 L of DI-water using dialysis tubing (benzoylated, cellulose dialysis tubing, molecular weight cut off 2,000, available form Sigma). The dialyzed portion was freeze dried to give about 940 mg of methacryloylated melimine as a fluffy white powder.

EXAMPLES 25 TO 27

Example 22 was repeated using the methacyloylated melamine of Example 24 in the amounts shown in Table 20, below. Lens properties were measured and are shown in Table 20. Standard deviations are shown in parenthesis

TABLE 20

| Property | Control 4 | Ex 25 | Ex 26 | Ex 27 |
|---|---|---|---|---|
| Methacryloylated Melimine added to 15 g of reaction mixture (mg) | 0 | 56.26 | 112.5 | 225.2 |
| Water Content (%) | 36.2(0.3) | 34.2(0.3) | 33.8(0.3) | 33.1(0.3) |
| Modulus (psi) | 80(17) | 101(12) | 103(13) | 111(13) |
| Elongation (%) | 210(99) | 189(74) | 174(69) | 205(49) |
| Tensile Strength (psi) | 71(37) | 77(35) | 68(25) | 82(18) |
| Toughness (psi) | 89(67) | 84.(60) | 67(50) | 90(37) |
| Contact Angle (adv. in packing) | 114(13) | 73(25) | 53(5) | 69(13) |

EXAMPLE 28

Lenses made in Examples 25 to 27 were removed from vials and washed three times in 5 mL of PBS for 5 minutes each wash. Lenses having the same substrate formulation, but without the methacryloylated melimine were used as a control. Four lenses were exposed to bacteria (P. aeruginosa or S. aureus) at 35° C. for the times shown in Table 21, below and analyzed as described in Example 2. Standard deviations are shown in parenthesis.

TABLE 21

| | | Ex 25 | Ex 26 | Ex 27 |
|---|---|---|---|---|
| | | P. aeruginosa (% redxn) | | |
| Time | 10 min. | 5 (15) | 12 (7) | −90 (113) |
| | 5 hrs | 78 (1) | 74 (2) | 78 (1) |
| | | S. aureus (% redxn) | | |
| Time | 10 min. | −39 (10) | 35 (27) | −156 (214) |
| | 5 hrs | −17 (101) | 38 (62) | 65 (2) |

What is claimed is:

1. A biomedical device at least one surface of which comprises a coating effective amount of at least one synthetic antimicrobial peptide comprising three segments A, B and C, in any order, wherein
   segment A is a peptide having the sequence SEQ ID NO. 1;
   segment B is a peptide having the sequence SEQ ID NO. 2; and
   segment C is a linking group of up to 10 amino acids, and which does not inhibit the antimicrobial activity of the peptide or induce toxicity in mammalian cells, and which includes 0 to about 10 amino acids.

2. The device of claim 1 wherein said device is selected from the group consisting of catheters, implants, stents, fluid collection bags, sensors, hydrogel bandages, tubing, carriers for antibiotic, diagnostic and therapeutic agents, and ophthalmic devices.

3. The device of claim 1 wherein the device is an ophthalmic device.

4. The device of claim 1 wherein segment C has a formula —HN—$(CR^1R^2)_n$—CO— wherein n is an integer between 1 and 21, $R^1$ and $R^2$ are independently selected from the group consisting of H, straight or branched alkyl groups having 1 to 4 carbon atoms, straight or branched hydroxyl groups having 1–2 carbon atoms, straight or branched alkylthio groups having 1 to 3 carbon atoms, carbamoyl groups having 1 to 3 carbon atoms, carboxy groups having 1 to 3 carbon atoms, primary and secondary amino groups having 1 to 4 carbon atoms and 1 to 3 nitrogen atoms, benzyl, phenol, phenyl indoles and N,N-pyrroles.

5. The device of claim 4 wherein n is an integer between 1 and 10 and at least one of $R^1$ and $R^2$ is H.

6. The device of claim 1, wherein the A and B segments are in terminal positions and segment C comprises up to 5 amino acids.

7. The device of claim 1, wherein the at least one surface comprises a coating effective amount of melimine, protattin and mixtures thereof.

8. The device of claim 7, wherein said melimine is L-melimine.

9. The device of claim 7, wherein said melimine is D-melimine.

10. The device of claim 1, wherein the surface further comprises a polymer selected from the group consisting of hydrogels, silicone hydrogels, polymers and copolymers of 2-hydroxyethylmethacrylate and mixtures thereof.

11. The device of claim 10 wherein the polymer is a hydrogel.

12. The device of claim 10 wherein the polymer is a silicone hydrogel.

13. The device of claim 10 wherein the polymer is a polymer or copolymer of 2-hydroxyethylmethacrylate.

14. The device of claim 13 wherein the copolymer of 2-hydroxyethylmethacrylate is a lightly crosslinked copolymer of 2-hydroxyethylmethacrylate.

15. The device of any of claims 1 to 3 or 4–14, wherein said device is a contact lens.

* * * * *